(12) United States Patent
Degertekin et al.

(10) Patent No.: US 8,766,459 B2
(45) Date of Patent: Jul. 1, 2014

(54) CMUT DEVICES AND FABRICATION METHODS

(75) Inventors: F. Levent Degertekin, Atlanta, GA (US); Gokce Gurun, Smyma, GA (US); Jaime Zahorian, Atlanta, GA (US); Michael Hochman, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 13/696,294

(22) PCT Filed: May 3, 2011

(86) PCT No.: PCT/US2011/034989
§ 371 (c)(1),
(2), (4) Date: Jan. 30, 2013

(87) PCT Pub. No.: WO2011/140082
PCT Pub. Date: Nov. 10, 2011

(65) Prior Publication Data
US 2013/0127065 A1      May 23, 2013

Related U.S. Application Data

(60) Provisional application No. 61/330,516, filed on May 3, 2010.

(51) Int. Cl.
*H01L 29/40*      (2006.01)
*H01L 23/52*      (2006.01)
*H01L 23/48*      (2006.01)

(52) U.S. Cl.
USPC ............... 257/777; 257/E21.614; 257/686; 257/723; 438/109; 438/667

(58) Field of Classification Search
CPC .................................................. H01L 25/0657
USPC .......... 257/E21.599, 685, 686, 723, 737, 774, 257/777, E21.614, E25.013; 438/113, 629, 438/637, 639, 667, 109
See application file for complete search history.

(56) References Cited

U.S. PATENT DOCUMENTS

| | | | |
|---|---|---|---|
| 7,781,238 B2 * | 8/2010 | Wodnicki et al. ............... | 438/17 |
| 7,835,207 B2 * | 11/2010 | Keeth et al. .................... | 365/200 |
| 7,969,009 B2 * | 6/2011 | Chandrasekaran ............ | 257/758 |
| 8,223,523 B2 * | 7/2012 | Jin et al. .......................... | 365/51 |
| 8,263,439 B2 * | 9/2012 | Marimuthu et al. .......... | 438/126 |
| 8,269,350 B1 * | 9/2012 | Chen et al. ..................... | 257/774 |

(Continued)

OTHER PUBLICATIONS

International Search Report and Written Opinion dated Sep. 29, 2011 for related PCT Application No. PCT/US2011/034989.

*Primary Examiner* — Chris Chu
(74) *Attorney, Agent, or Firm* — Troutman Sanders LLP; Ryan A. Schneider; Christopher W. Glass

(57) ABSTRACT

Capacitive micromachined ultrasonic transducer ("CMUT") devices and fabrication methods are provided. The CMUT devices can include integrated circuit devices utilizing direct connections to various CMOS electronic components. The use of integrated connections can reduce overall package size and improve functionality for use in ultrasonic imaging applications. CMUT devices can also be manufactured on multiple silicon chip layers with each layer connected utilizing through silicon vias (TSVs). External power connections can be provided if high biasing voltages are required. Forward and side looking CMUT arrays can be manufactured for use in a variety of ultrasound technologies.

19 Claims, 10 Drawing Sheets

(56) References Cited

U.S. PATENT DOCUMENTS

| | | | |
|---|---|---|---|
| 8,338,294 B2 * | 12/2012 | Sadaka | 438/667 |
| 8,349,729 B2 * | 1/2013 | Barth et al. | 438/637 |
| 8,476,771 B2 * | 7/2013 | Scheuermann et al. | 257/774 |
| 8,519,543 B1 * | 8/2013 | Song et al. | 257/774 |
| 8,552,569 B2 * | 10/2013 | Lee | 257/777 |
| 8,560,982 B2 * | 10/2013 | Rahman | 716/100 |
| 2005/0094490 A1 | 5/2005 | Thomenius et al. | |
| 2005/0148132 A1 | 7/2005 | Wodnicki | |
| 2005/0275084 A1 * | 12/2005 | Kirby et al. | 257/697 |
| 2007/0264732 A1 | 11/2007 | Chen | |
| 2008/0054489 A1 * | 3/2008 | Farrar et al. | 257/777 |
| 2009/0182229 A1 | 7/2009 | Wodnicki | |
| 2009/0250729 A1 | 10/2009 | Lemmerhirt et al. | |
| 2009/0261460 A1 * | 10/2009 | Kuan et al. | 257/660 |
| 2009/0283898 A1 * | 11/2009 | Janzen et al. | 257/698 |
| 2009/0321947 A1 * | 12/2009 | Pratt | 257/777 |
| 2011/0175215 A1 * | 7/2011 | Farooq et al. | 257/686 |

\* cited by examiner

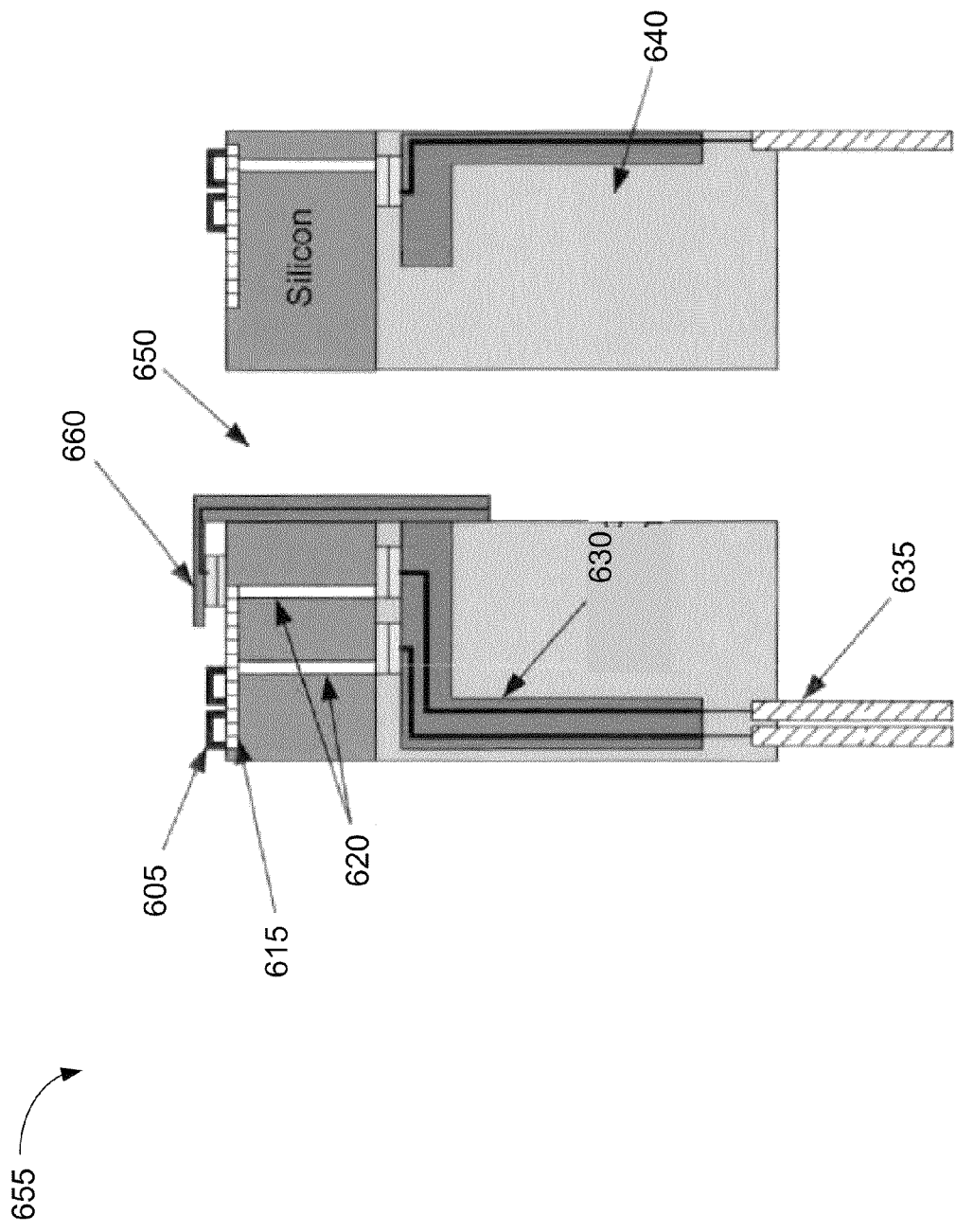

CMUT DEVICES AND FABRICATION METHODS

RELATED APPLICATIONS AND PRIORITY CLAIM

This application is a United States National Stage Application of International Patent Application Serial No. PCT/US2011/034989, filed 3 May, 2011, which claims the benefit of U.S. Provisional Application No. 61/330,516 filed 3 May 2010, the entire contents and substance of these applications hereby incorporated by reference.

STATEMENT REGARDING FEDERALLY SPONSORED RESEARCH OR DEVELOPMENT

This invention was made with Government support under Project Numbers E25-C54 and 2506C54, awarded by the National Institute of Health. The Government has certain rights in the invention

BACKGROUND OF THE INVENTION

1. Technical Field

The present invention relates generally to fabricating capacitive micromachined ultrasonic transducers ("CMUTs"), CMUT imaging arrays, and electrical interconnect structures for catheter based devices using CMUT imaging arrays.

2. Background of Related Art

CMUTs combine mechanical and electronic components in very small packages. The mechanical and electronic components operate together to transform mechanical energy into electrical energy and vice versa. Because CMUTs are typically very small and have both mechanical and electrical parts, they are commonly referred to as micro-electronic mechanical systems ("MEMS") devices. CMUTs, due to their miniscule size, can be used in numerous applications in many different technical fields, including medical device technology.

One application for CMUTs within the medical device field includes soft tissue and vascular imaging. This type of imaging can be carried out using an array with CMUTs mounted, for example, on a flexible catheter. The quality of the image produced is somewhat dependent on the size of the array, the acoustic power radiated to the medium, and the control over certain components of the CMUTs (e.g., diaphragm position) during transmission and reception of ultrasonic energy. The size of vessels that can be imaged using this technology, on the other hand, is limited by the size of the CMUT array and, accordingly, the catheter size. A smaller CMUT array enables smaller vessels and surrounding tissues to be imaged, reduces the obstruction of blood flow and makes it easier to maneuver.

In intravascular ultrasound (IVUS) imaging, it is important to have a small diameter catheter to image small coronary arteries. As a result, regardless of what technology is used (e.g., PZT or CMUT based arrays), the electrical interconnect scheme between the ultrasound array and the processing electronics becomes important in implementation, particularly for forward looking IVUS imaging. Since the forward looking IVUS catheter diameter is preferably on the order of 1-2 mm, it is desirable to use as much of the frontal area of the catheter as possible for ultrasound generation and reception. The use of a larger array can increase power levels and also improve image resolution.

CMUTs 100 manufactured using complementary metal-oxide-semiconductor (CMOS) manufacturing techniques are suitable for imaging very small blood vessels such as capillaries in terms of size. However, as shown in FIG. 1, significant numbers of connections 105 are required between the CMUTs 110 and the front-end electronics 115 through external, flexible interconnects 105. In addition, because the electronics 115 are generally manufactured on a separate chip, large numbers of these external connections 105 are required to connect each of the CMUTs to, for example, a duplexer. This results in a package 100 with an undesirably small CMUT 110 array, to keep the package small enough to be useful, or an array that is larger than necessary due to the external connections 105. In addition, these arrays 100 can also require a cover, or other structure, to cover the external wiring to prevent snags and damage to the subject artery.

What is needed, therefore, is a method for connecting the various electronic components in a manner that maximizes the CMUT array, while minimizing array cross-section using an internal connection scheme.

Additionally, there is a need in the art for fabricating CMUTs and CMUT arrays utilizing existing and inexpensive CMOS silicon chip manufacturing methods.

Additionally, the CMUT and associated electronics can be fabricated on the same chip, or on adjacent silicon layers, to minimize the number of external interconnects required.

Additionally, the transmit and receive electronics may require different CMOS processes, such as high voltage and low voltage processes, thus a compact interconnect scheme between the CMUT, low voltage CMOS and high voltage CMOS chips is needed while minimizing the overall size of an IVUS catheter.

It is to the provision of such CMUT fabrication and CMUT imaging array fabrication that the embodiments of present invention are primarily directed.

BRIEF SUMMARY OF THE INVENTION

Embodiments of the present invention relate to electronic manufacturing methods and components based on through wafer via technology for CMUT and CMUT-on-CMOS type forward and side looking ultrasound imaging catheters. These methods and components can use combinations of through wafer vias and flexible interconnects to connect CMUT and CMOS electronics, and CMUT bias connections. The CMOS electronics and CMUT bias lines can then be externally connected using coax or other small cables which span the remainder of the catheter.

Embodiments of the present invention, therefore, can comprise an integrated circuit comprising a first silicon chip comprising one or more CMUTs and one or more additional silicon chips each comprising one or more CMOS electronic devices. The first silicon chip and the one or more additional silicon chip can be electrically connected using one or more through silicon vias (TSVs) disposed in the silicon chips. In some embodiments, the CMOS electronic devices can comprise one or more buffers, multiplexers, and/or amplifiers. In some embodiments, the additional silicon chips can be used to create a high voltage chip and a low voltage chip. This can isolate high voltage electronics from low voltage electronics to ease manufacturing and minimize interference.

Embodiments of the present invention can also comprise an integrated circuit comprising a plurality of CMUT silicon chips, each comprising one or more CMUTs and a plurality of CMOS silicon chips, each comprising one or more CMOS electronic devices to form a 2-D CMUT array. Each of the plurality of CMUT silicon chips can be electrically connected to one of the plurality of CMOS silicon chips using one or more through silicon vias (TSVs) disposed in each of the plurality of CMUT silicon chips and each of the plurality of CMOS silicon chips.

The integrated circuit can further comprise one or more cables for inputting and receiving signals from the integrated circuit. In some embodiments, the cables can act as a guide wire, or can be housed by a separate guide wire. The guide wire can be used to manipulate the three-dimensional CMUT array.

Other embodiments of the present invention can comprise an integrated circuit including one or more CMOS electronic devices disposed on a front side of a substrate, one or more CMUTs disposed on the front side of the substrate, and two or more vias for providing an electrical connection from the front of the substrate to the back of the substrate. In some embodiments, the one or more CMUTs can be deposited or printed directly on top of, and in electrical communication with, the one or more CMOS electronic devices. One or more printed circuit traces can electrically connect the one or more CMUTs, the one or more CMOS electronic devices, or both, to the two or more vias. In some embodiments, the CMOS electronic devices can also comprise one or more vias manufactured into otherwise unused areas of the chip.

The CMUTs can each comprise a bottom electrode disposed on the front side of the substrate, a diaphragm for transmitting and receiving ultrasonic waves, and two or more diaphragm electrodes disposed in, or on, the diaphragm for shaping the diaphragm. The diaphragm electrodes can enable the diaphragm to have multiple positions optimized for receiving and transmitting ultrasonic waves. In some embodiments, the circuit can further comprise an external flexible interconnect to provide a biasing voltage to the two or more electrodes. In other embodiments, a mass load can be disposed proximate the diaphragm to adapt the diaphragm to receive or transmit energy at a predetermined frequency.

Embodiments of the present invention can also comprise a method of manufacturing an integrated circuit comprising depositing one or more CMOS electronic components to form a CMOS electronics layer on a front side of a substrate, depositing an oxide or nitride based isolation layer over the CMOS electronic components, etching, or drilling one or more through silicon vias (TSVs) through the substrate, depositing dielectric material into the one or more TSVs, electroplating the one or more TSVs to form electrical connections, opening the isolation layer (e.g., by etching) on the CMOS electronics layer to enable electrical connection to the CMOS electronics, and depositing one or more CMUT electronic components on the isolation layer such that the CMUT electronic components are in electrical contact with the CMOS electronic components.

The method of manufacture can further comprise covering the back side of the substrate with an oxide or nitride based isolation layer. In some embodiments, the etching step can further comprise etching one or more pathways to enable connection between the CMOS electronic components and the TSVs. Electrical connections such as, for example and not limitation, metal traces, can be used to connect the CMOS electronic components to the TSVs. In some embodiments, further processing may be desirable including, but not limited to, removing the protection layer from the back side of the substrate and connecting one or more electrical components to the back side of the TSVs. The one or more electrical components can include, for example and not limitation, one or more cables for inputting and receiving signals from the integrated circuit and/or additional CMOS components.

These and other features as well as advantages, which characterize the various preferred embodiments of present invention, will be apparent from a reading of the following detailed description and a review of the associated drawings.

DETAILED DESCRIPTION OF PREFERRED EMBODIMENTS

Figure 1:
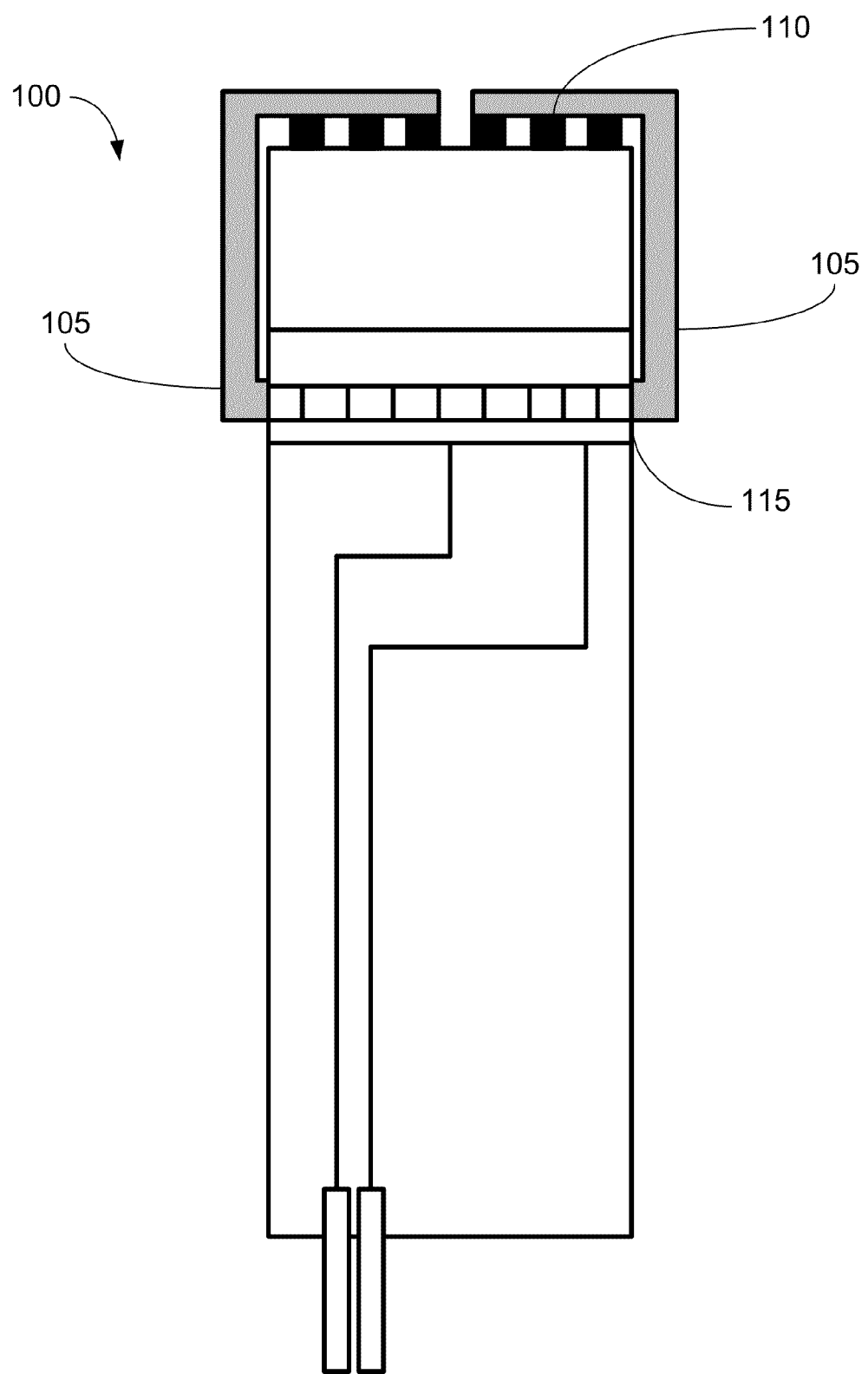
FIG. 1 illustrates a cross-sectional view of a conventional CMUT with external electronic connections.

CMUTs have been developed as an alternative to piezoelectric ultrasonic transducers, particularly for micro-scale and array applications. CMUTs are typically surface micromachined and can be fabricated into one or two-dimensional arrays and customized for specific applications. CMUTs can have performance comparable to piezoelectric transducers in terms of bandwidth and dynamic range, but are generally significantly smaller.

A CMUT typically incorporates a one or more electrodes disposed within a membrane suspended above a conductive substrate or one or more bottom electrodes coupled to, or proximate, a lower substrate. Adhesion layers or other coatings can optionally be disposed between the substrate and the bottom electrode. The membrane can have elastic properties enabling it to fluctuate in response to stimuli. For example, stimuli can include, but are not limited to, external forces exerting pressure on the membrane and electrostatic forces applied through the one or more electrodes.

CMUTs are often used to transmit and receive acoustic waves. To transmit an acoustic wave, an AC signal and/or a large DC bias voltage are applied to the one or more CMUT electrodes disposed within the CMUT membrane. Alternatively, the voltages can be applied to the one or more bottom electrodes. The DC voltage can pull down the membrane to a position where transduction is efficient and the CMUT device response can be linearized. The AC voltage can cause motion in the membrane at a desired frequency to generate an acoustic wave in a surrounding medium, such as soft tissue, gases, or fluids.

To receive an acoustic wave, on the other hand, a DC biasing voltage can be applied to the membrane to pull the membrane close to the bottom substrate. The capacitance change between the one or more CMUT electrodes can be measured when an impinging acoustic wave causes motion in the CMUT membrane. Pulling the membrane down into close proximity with the bottom substrate increases the sensitivity of the CMUT and improves response.

Due to the tiny size of a single CMUT a plurality of CMUTs can be assembled to form a CMUT array. The CMUT array can, in turn, be used in a variety of ultrasound and imaging applications. The arrays can, in fact, be made small enough to pass through veins and arteries to provide close proximity imaging and mapping of neighboring soft tissues and the blood vessels themselves. These images can be useful for in a variety of applications including diagnosis and treatment.

The materials described hereinafter as making up the various elements of the present invention are intended to be illustrative and not restrictive. Many suitable materials that would perform the same or a similar function as the materials described herein are intended to be embraced within the scope of the invention. Such other materials not described herein can include, but are not limited to, materials that are developed after the time of the development of the invention, for example. The dimensions listed in the various drawings are for illustrative purposes only and are not intended to be limiting. Other dimensions and proportions are contemplated and intended to be included within the scope of the invention.

Referring now the drawings, in which like numerals represent like elements, embodiments of the present invention are herein described.

As discussed above, and shown in FIG. 1, one problem with existing CMUT arrays 100 is that using conventional manufacturing techniques requires that the CMUTs 110 and the corresponding CMOS electronics 115 (CMOS) be mounted on separate chips and thus, in separate locations on the apparatus 100. Each CMUT 110 must then be connected to the CMOS electronics 115 using multiple external flexible interconnects 105. This increases the diameter of the apparatus 100, which becomes a limiting factor for use with, for example and not limitation, very small blood vessels (e.g., capillaries). What is needed, therefore, is a CMUT array and a method for manufacturing same that minimizes these interconnects and the overall size of the imaging sensor.

Figure 2:
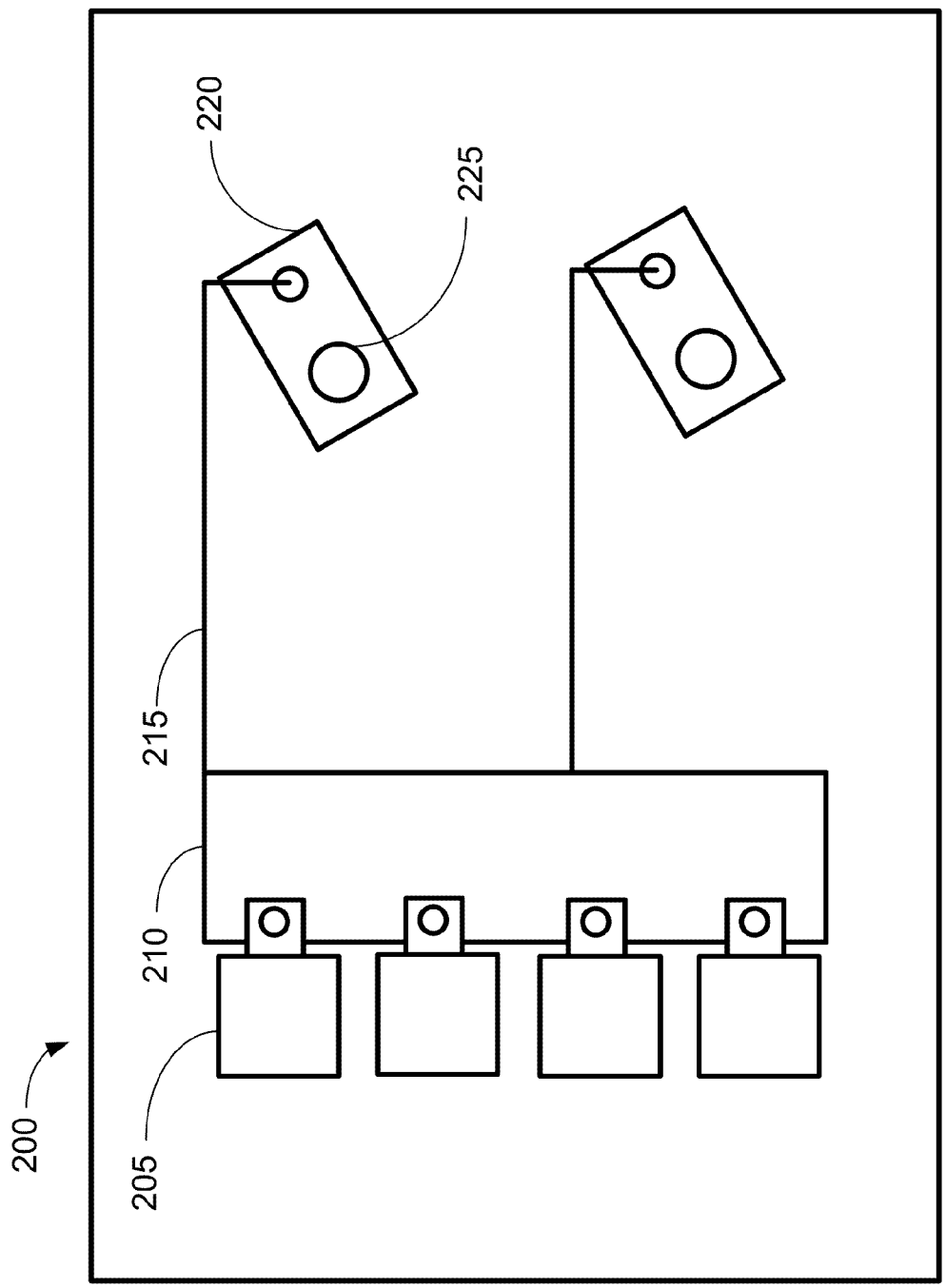
FIG. 2 depicts a top view of an internally connected CMUT array, in accordance with some embodiments of the present invention.
Figure 3:
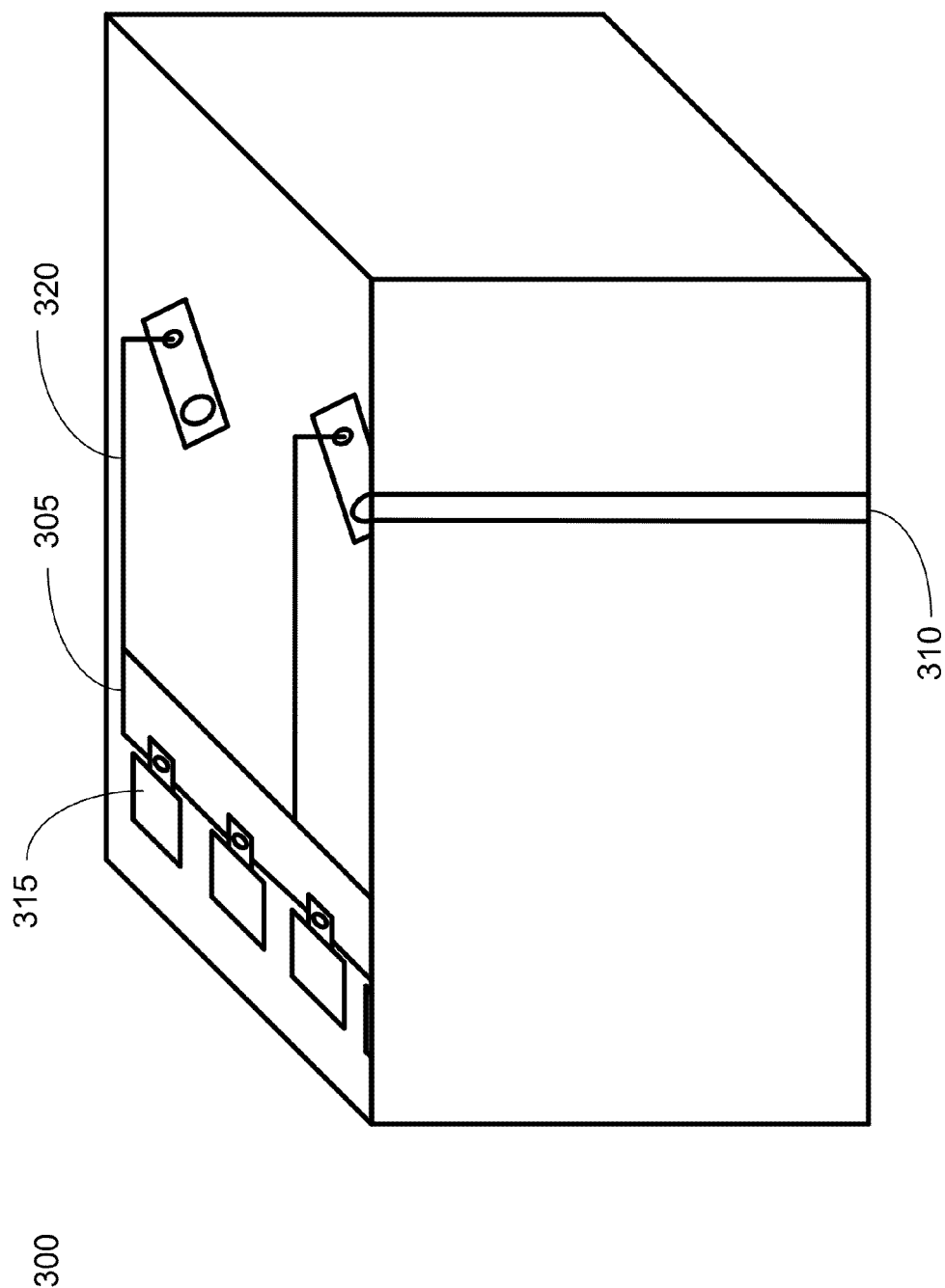
FIG. 3 depicts a perspective, cross-section view of the internally connected CMUT array of FIG. 2, in accordance with some embodiments of the present invention.

In conventional CMUT configurations 100, therefore, the CMOS electronics 115 are located separately on the apparatus 100 from the CMUTs 110. This necessitates the use of multiple flexible interconnects 105 (e.g., one interconnect 105 per CMUT 110) to connect the CMUT 110 and CMOS 115 electronics. To address this issue, as shown in FIGS. 2 and 3, embodiments of the present invention relate to an ultrasonic transducer 200 comprising one or more CMUTs 205 in an integrated circuit with various CMOS electronics 210.

The CMOS electronics 210 can comprise, for example and not limitation, duplexers, amplifiers, and buffers. The CMOS electronics 210 can enable the various signals from the one or more CMUTS 205 to be combined and processed. This enables the number of output lines 215 from the electronics 210 to be significantly reduced. Multiple CMUT 205 outputs, for example, can be combined and prioritized using one or more multiplexers to reduce the number of outputs 215 required to two outputs 215, in some embodiments. The outputs 215 can be connected using, for example and not limitation, pad connections 220, which can be connected externally using through silicon vias 225 through the chip substrate 230.

This configuration also enables the CMUTs 205 and CMOS electronics 210 to be located on the front of the chip 200, while most or all of the electrical connections to the chip 200 can be made on the back of the chip 200. This can be useful, for example, to maximize the number of CMUTs 205 on the front of the chip 200 for improved resolution. This can also minimize the interaction between the electronics 205, 210 and the electrical connections 215, 225 (e.g., interference caused by biasing voltages).

Figure 4:
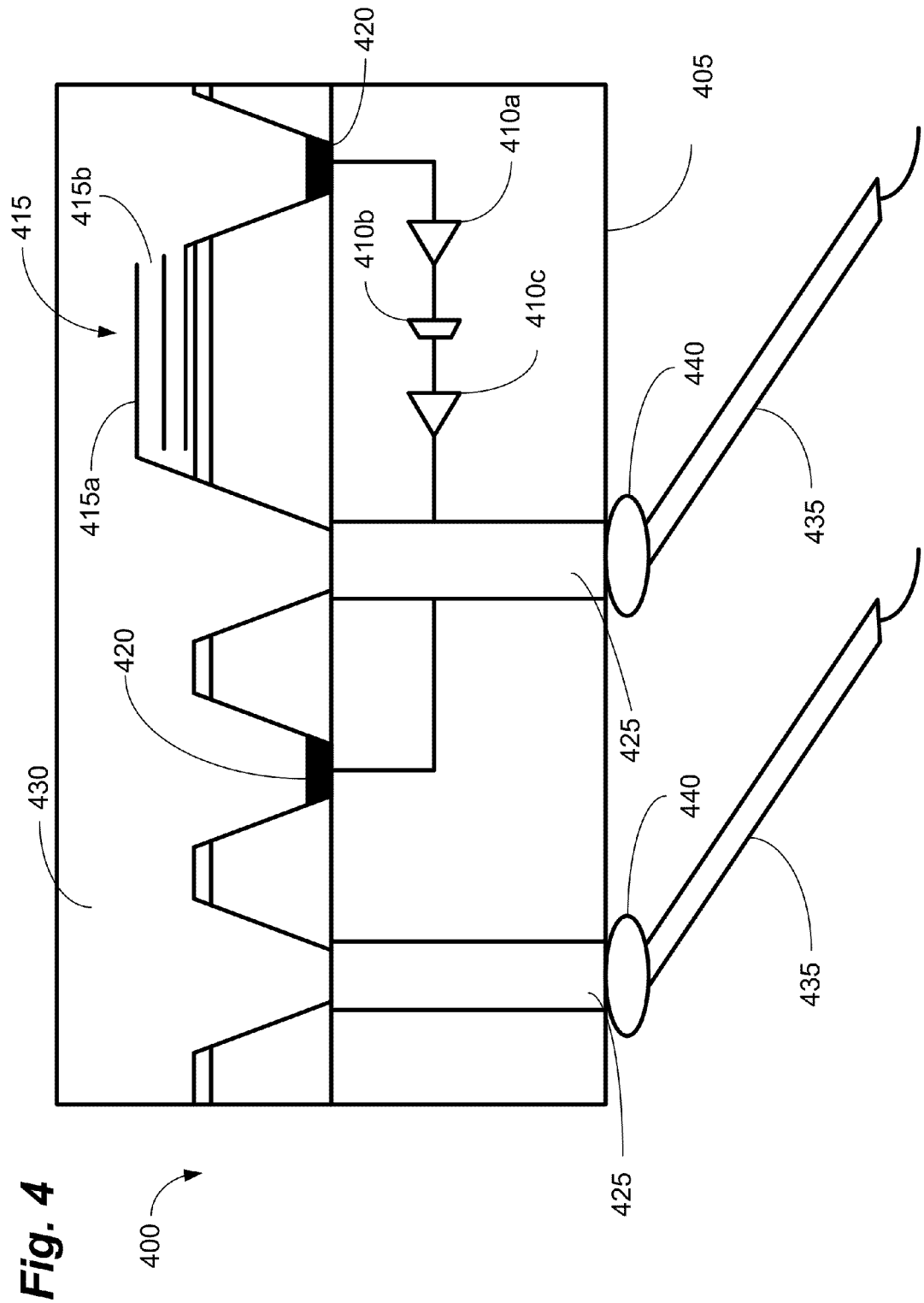
FIG. 4 depicts a top view of another internally connected CMUT array, in accordance with some embodiments of the present invention.
Figure 5A:
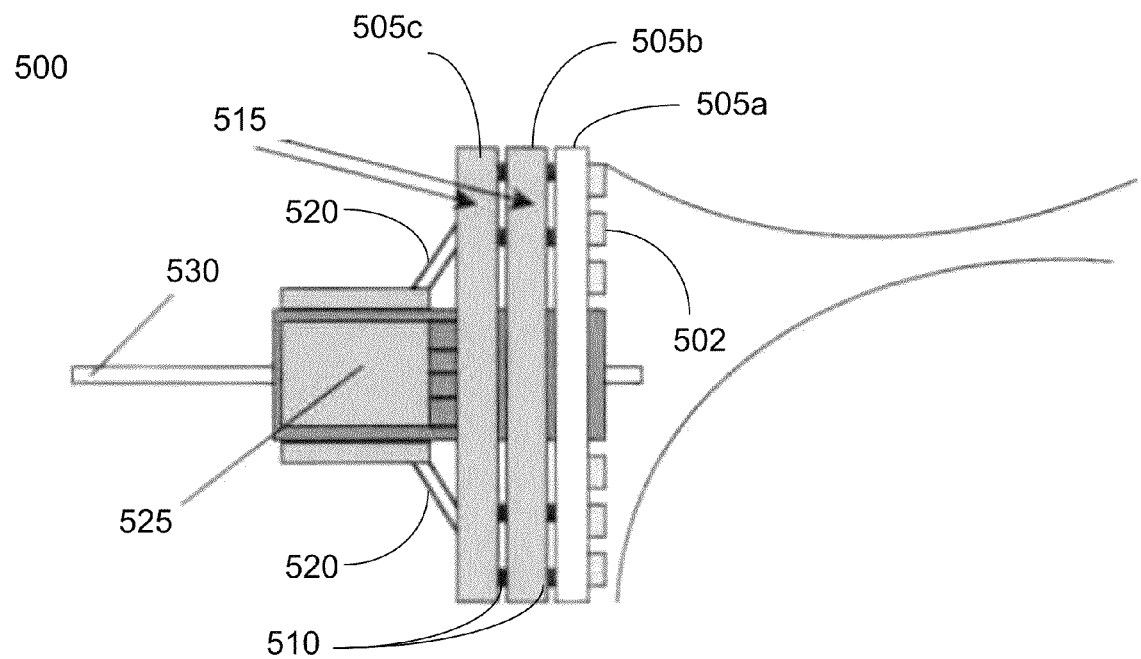
FIG. 5 depicts a perspective, cross-section view of the internally connected CMUT array of FIG. 4, in accordance with some embodiments of the present invention.
Figure 5B:
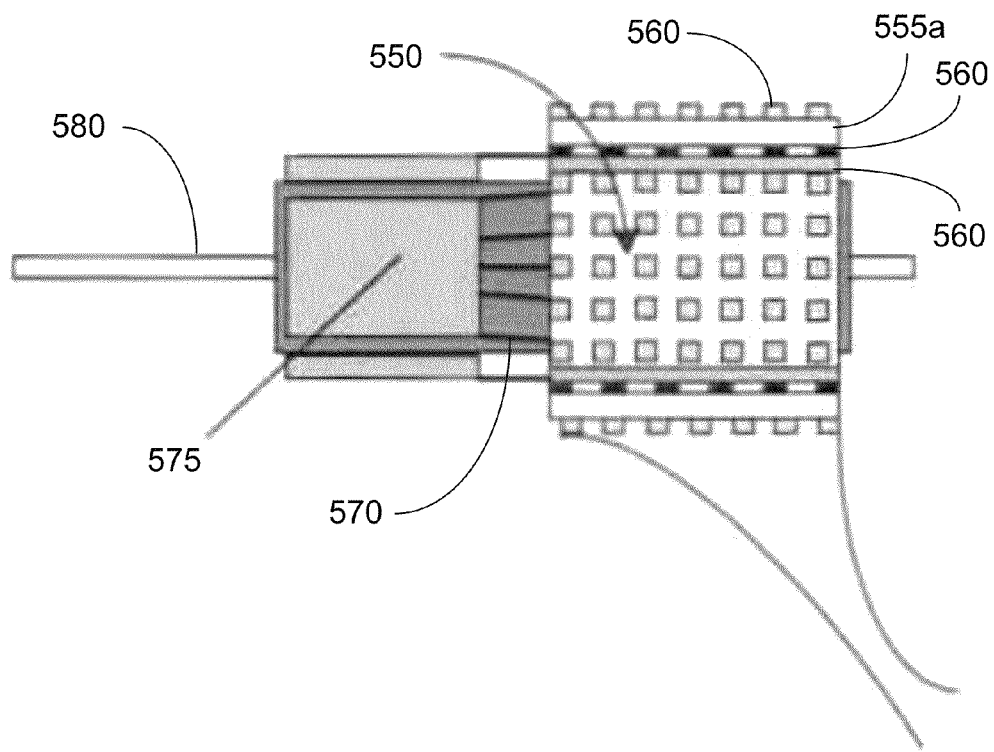

Referring now to FIGS. 4 and 5, embodiments of the present invention, therefore, can further comprise low temperature processes to fabricate through silicon vias (TSV) 410 on custom CMOS wafers 405 before CMUT 415 processing. As shown in FIG. 4, custom CMOS wafers 405 can be processed with vias 410 located in regions without any electronic components as defined during the CMOS layout. The CMOS components 405 can be protected with, for example and not limitation, an isolation later comprising an oxide or nitride. In some embodiments, the back side of the wafer 400 can be protected with oxide or nitride as well if electrostatic effects are of concern in a particular application. Through-Silicon Vias (TSVs) 410 can be etched through the CMOS chip 405 and/or the substrate 430 and a dielectric can be deposited therein. In some embodiments, electroplating can be used to form the via 410. The low voltage bias used during electroplating generally will not affect the CMOS electronics 405.

For CMUT 415 processing, the previously deposited isolation layer can be etched to create a path for CMUT 415 to CMOS 405 connection. In some embodiments, additional openings can be made to connect the CMOS output lines 420 to additional through-wafer vias 425. Using a metallization process, the CMUTs 415 can be defined and connected to CMOS electronics 405. In addition, connections can be made between the CMOS electronics 405 and the vias 410 through, for example and not limitation, a simple metal trace. If necessary, electrical passivation can be removed from the backside of the wafer 400 to enable flex tape bonding.

Additional CMUT 415 processing can be accomplished to provide a variety of CMUT 415 features. Multiple element electrodes, for example, can provide additional CMUT diaphragm control. Diaphragm weighting can modify diaphragm frequency response. These features and methods are discussed in detail in, for example and not limitation, U.S. patent application Ser. No. 11/068,129 entitled, "Harmonic CMUT Devices and Fabrication Methods" filed 28 Feb. 2005; U.S. patent application Ser. No. 11/077,841, entitled, "Asymmetric Membrane CMUT Devices and Fabrication Methods" filed 11 Mar. 2005; and U.S. patent application Ser. No. 11/068,005, entitled "Multiple Element Electrode CMUT Devices and Fabrication Methods," filed 28 Feb. 2005, each of which are incorporated herein by reference as if fully set forth below.

In some embodiments, as better shown in FIG. 5, the vias 410 can be manufactured directly into the CMOS electronics chip 405. The vias 410 can be created, for example, during CMOS chip 405 manufacturing by etching, or other means. The CMOS chip 405 can then be protected with an isolation layer (e.g., an oxide or nitride layer) until CMUT 415 processing begins. In some embodiments, as shown, the CMUTs 415 can then be manufactured directly on top of the CMOS chip 405. Connection between the CMUT 415 and CMOS electronics 405 can be achieved by opening connections at the vias 410 in the isolation layer.

In still other embodiments, the CMOS chip 405 can be manufactured with areas that do not contain electronics. In this configuration, vias 410 can be formed on the CMOS chip 405 after the CMOS electronics are fabricated thereon. In this case, the layout of CMOS electronics is such that some area on the CMOS chip 405 is left without electronics to enable vias 410 to be created (e.g., by drilling holes in the chip) without damaging the electronics. In this case, the CMOS electronics 405 can be isolated with a dielectric layer, the vias 410 can be formed, and CMUT 415 manufacturing can continue. The connections between the CMOS electronics 405 and the CMUTs 415 can be made by opening regions in the isolation layer and depositing and patterning conductive layers.

Figure 6A:
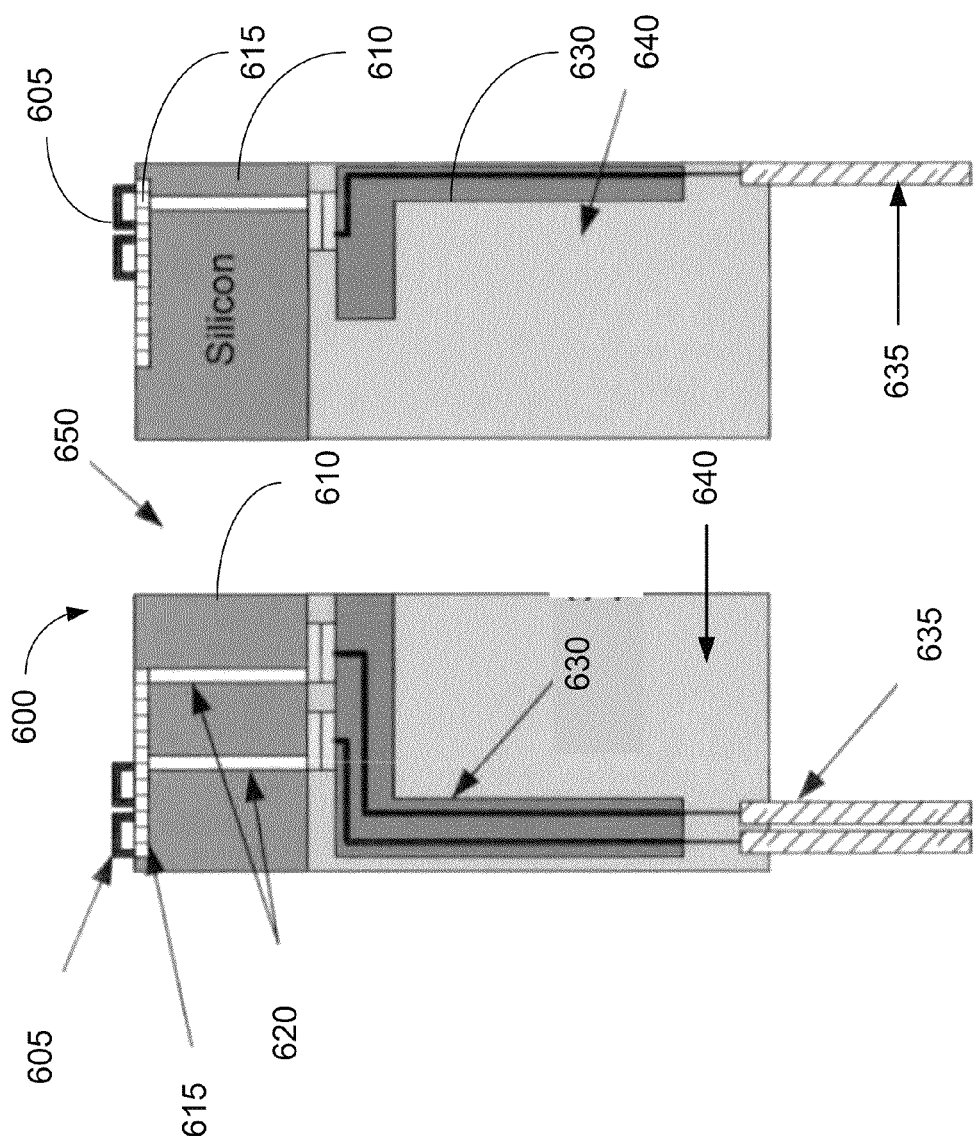
FIG. 6 depicts a cross-section view of an internally connected CMUT array including connection leads, in accordance with some embodiments of the present invention.

FIG. 6 depicts one possible CMUT on CMOS configuration, in accordance with some embodiments of the present invention. The custom CMOS chip 600 can comprise a silicon substrate 605 onto which the CMUT and CMOS electronics can be formed and integrated. The CMOS electronics 605 can comprise, for example and not limitation, one or more amplifiers 610a, multiplexers 610b, and buffers 610c for signal processing and combination. This can enable the signals from the one or more CMUTs 615 to be combined, thus minimizing the number of external connections required.

The CMUT components 615 can comprise, for example and not limitation silicon dioxide and can be deposited on the silicon chip 605 above the CMOS electronics 610. The CMUT can comprise a diaphragm 615a, one or more electrodes 615c, and a vacuum gap 615b that enable the CMUT 615 to send and receive ultrasonic waves. The CMUT 615 can be connected to the CMOS electronics 610 using a metal deposition layer 620, which can be, for example and not limitation, aluminum, gold, or copper. The chip 600 can be coated with a dielectric polymer layer 630 (e.g., silicon nitride) for protection if desired.

The silicon substrate 605 can further comprise one or more vias 625. In addition, because the CMUT 615 signals have been processed and combined, the number of outputs can be greatly reduced. As shown, therefore, the CMUT signals can be combined and connected using two leads 635 connected to the vias 625 using, for example and not limitation, metalized pads 640.

Figure 7:
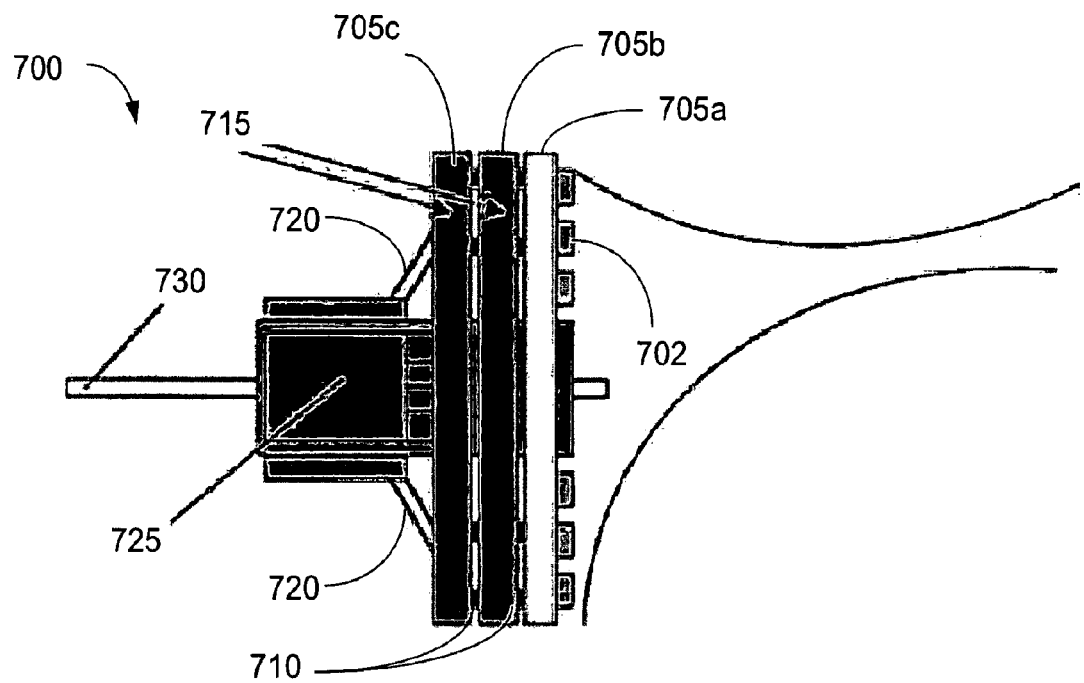
FIG. 7 depicts a side view of an internally connected, forward-looking CMUT array, in accordance with some embodiments of the present invention.

As shown in FIG. 7, embodiments, of the present invention can comprise a forward looking ultrasound array 700. In some embodiments, it may be desirable to maximize the number of CMUTs 702 on the top layer of the array 700. To this end, multiple chip layers 705a, 705b, 705c can be stacked and connected using vias 710. In this configuration, the number of CMUTS 702 on the top chip layer 705a can be maximized, while the necessary CMOS electronics 715 can be located on addition chips 705b, 705c, as necessary. The chips 705a, 705b, 705c can be, for example and not limitation, silicon discs bonded together and connected with one or more vias 710. This can be useful, for example, to increase the power and sensitivity of a forward-looking intravascular ultrasound imaging catheter.

High and low voltage electronics can require different manufacturing techniques. As a result, in some embodiments, the additional chips 705b, 705c can be used to create a high voltage chip 705b and a low voltage chip 705c. In this configuration, the high voltage chip 705b can comprise a variety of high voltage CMOS electronics 715b to, for example, drive the CMUTS 702 during transmission of ultrasonic energy. The low voltage chip 705c, on the other hand can comprise low voltage CMOS electronics 715c for ultrasonic reception. In this configuration, both high 715b and low 715c voltage electronics can be connected to the CMUTs 702 using multiple vias 710. In addition to overcoming the previously discussed manufacturing difficulties, this can prevent, for example, interference between the electronics 715b, 715c and between the electronics 715b, 715c and the CMUTs 702. Of course, the position of the respective chips 705b, 705c is arbitrary and additional chips can be incorporated to house additional CMOS electronics and connections as desired.

As shown, integrated CMOS electronics 715 can be incorporated into as many additional chip layers 705b, 705c as is necessary to house the desired electronics 715. In this configuration, while additional vias 710 are required to make the interchip connections, minimal external connections 720 are used because the signals have been, for example, processed and combined by the onboard electronics 715. In some embodiments, the external connections 720 can be used to connect the chip 700 to additional electronics 725 and/or one or more output leads 730. In some embodiments, the output leads 730 can comprise, or be housed in, the guide wire used to manipulate the chip 700.

Figure 8:
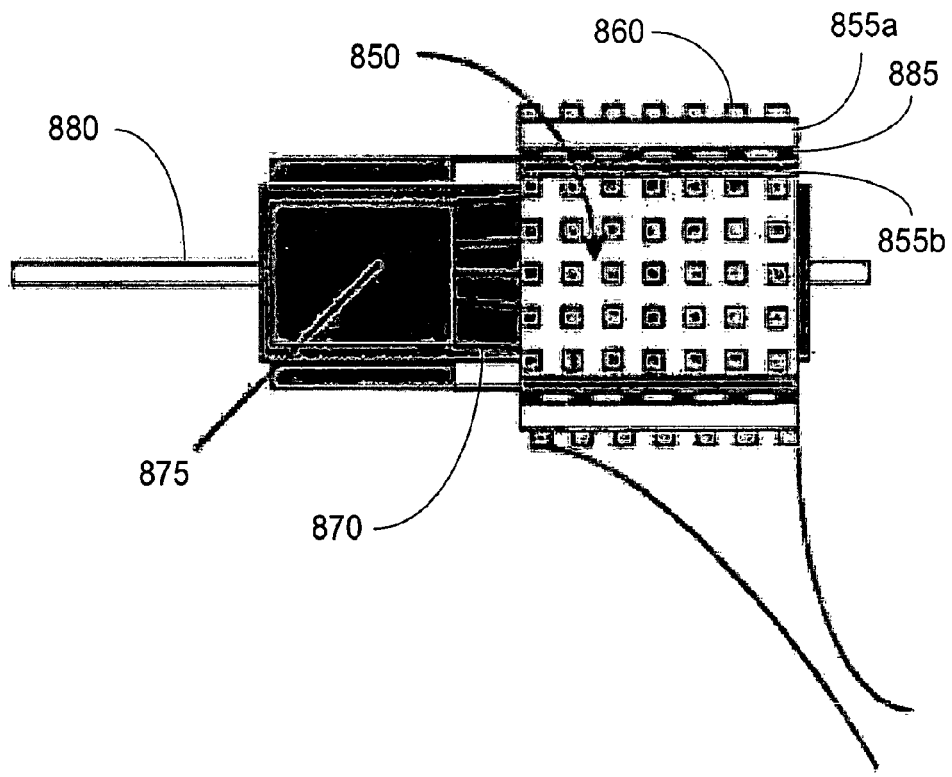
FIG. 8 depicts a side view of an internally connected, side-looking CMUT array, in accordance with some embodiments of the present invention.

As shown in FIG. 8, embodiments, of the present invention can further comprise a multi-dimensional ultrasound array 850. Similar to the forward-looking array 700, a chip layer 855a containing one or more CMUTs 860 can be connected using one or more vias 885 to additional chip layers 855b containing additional CMOS electronics. After processing, the signals can be connected using a minimum number of external connections 870. In some embodiments, the array 850 can comprise additional electronics 875 to provide additional signal processing. The array 850 can ultimately be connected using one or more leads 880. As before, the leads 880 can also serve as a guide wire, or can be housed therein.

Figure 9:
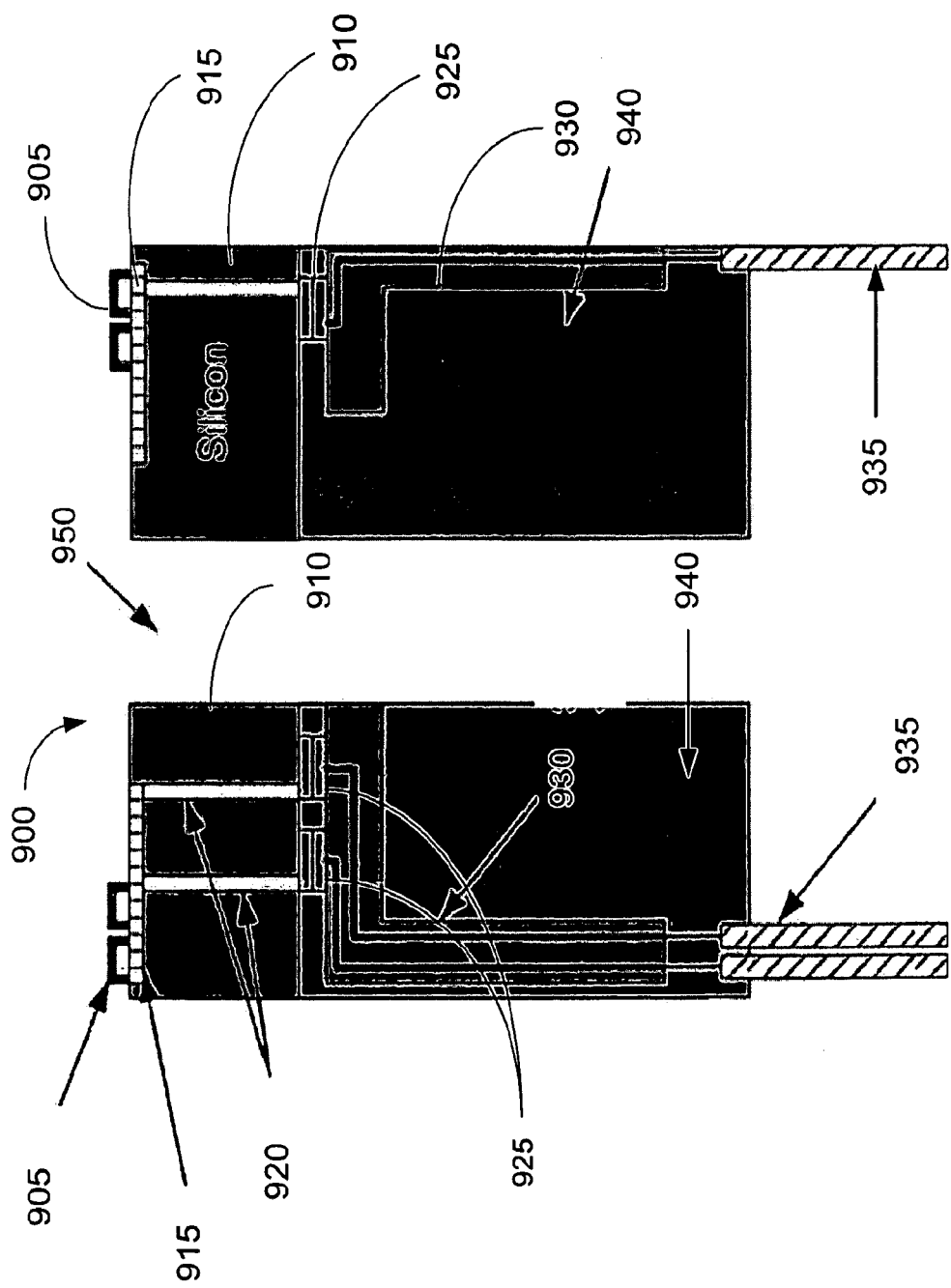
FIG. 9 depicts a cross-sectional view of an internally connected, forward-looking CMUT array, in accordance with some embodiments of the present invention.

FIG. 9 depicts a cross-section view of a forward-looking, intravascular ultrasound probe 900, in accordance with some embodiments of the present invention. The probe 900 can comprise a plurality of CMUTs 905 disposed in an array on the top surface of the probe 900. The CMUTs 905 can be manufactured on a silicon substrate 910 to form a custom CMUT/CMOS chip 910. In this configuration, the CMUTs 905 can be in direct connection with the CMOS chip 915. The silicon chip 910 and/or the CMOS chip 915 can comprise one or more vias 920 configured to connect the output from the CMOS electronics 915 to, for example, one or more metal connection pads 925.

In some embodiments, the metal connection pads 925 can, in turn, be connected to one or more external connections such as, for example and not limitation, flexible interconnects 930. The flexible interconnects 930 can be connected externally to one or more suitable conductors 935 including, but not limited to, coax cables. This configuration maximizes the number of CMUTs 905 in the array 900 and eliminates external connections on the top and sides of the array 900. In this manner, the probe 900 can have a minimal cross section and can be rounded and/or smoothed to facilitate use inside, for example and not limitation, small capillaries.

In some embodiments, the probe can comprise an opening 950 to enable a guide wire to be connected to the probe 900. This can enable the probe 900 to be manipulated during use. In some embodiments, the guide wire can house the conductors 935 and/or other cables and electronics. In some embodiments, the probe 900 can further comprise a cover, or other means, to further protect the electronics and to present a smooth, rounded profile. The probe 900 can further comprise structural support 940 to provide a substantially stiff platform onto which the electronics and other components can be mounted. The support 940 can comprise, for example and not limitation, silicon, plastic, or metal. In some embodiments, portions of the support 940 can be rounded, or otherwise shaped, to ease removal of the probe 900 and prevent vascular damage.

Figure 10:
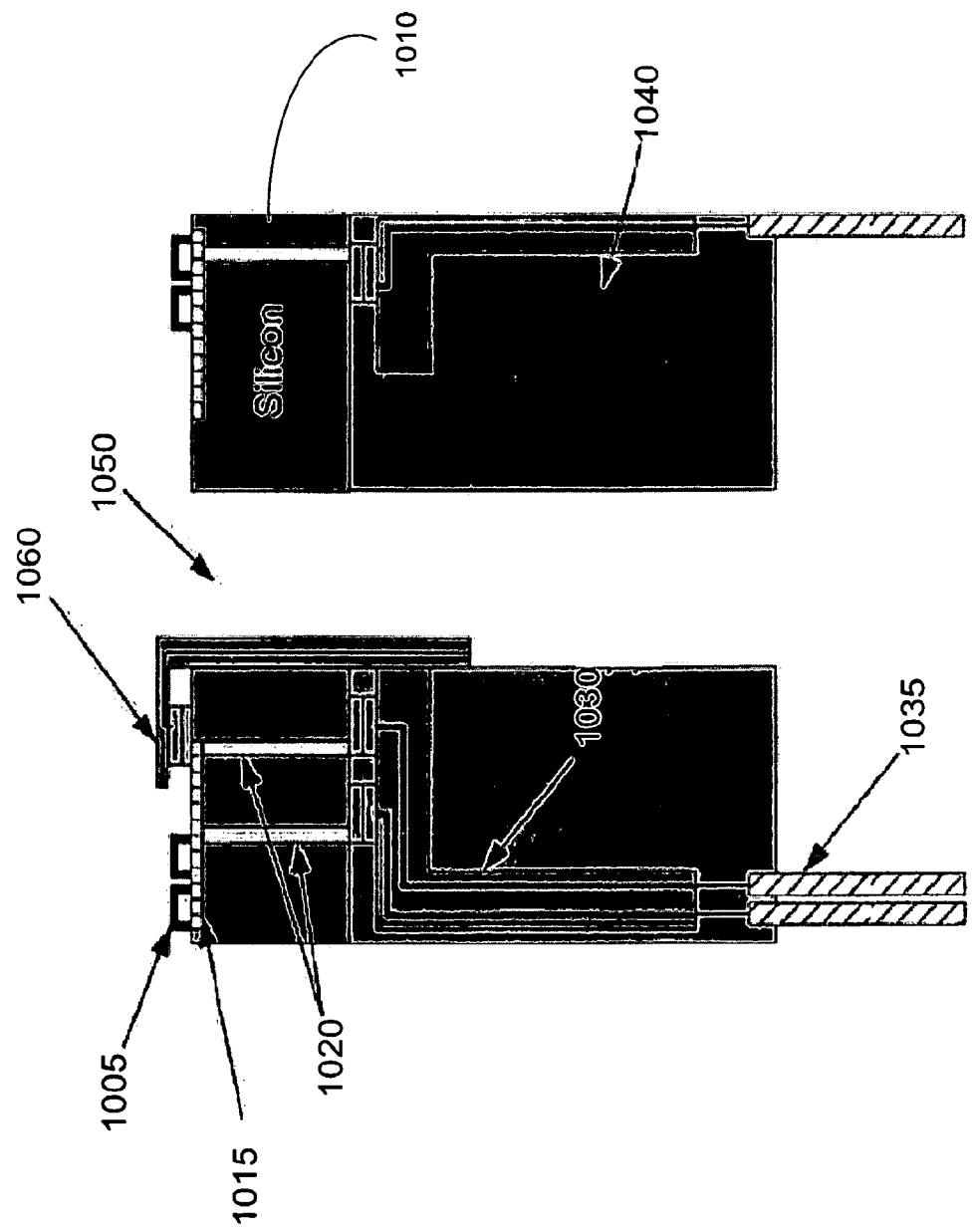
FIG. 10 depicts a cross-sectional view of an internally connected, forward-looking CMUT array with an external power cable, in accordance with some embodiments of the present invention.

In some embodiments, as shown in FIG. 10, it may be necessary, or desirable, to provide fairly substantial electrical loads to the CMUT array 1005. This can be useful, for example and not limitation, to provide a biasing voltage to the CMUT 1005 diaphragm electrodes to place the diaphragm in an improved position for transmission or reception. In some embodiments, therefore, it may be desirable to provide an external power cable 1060 to the CMUT array 1005. In other words, the internal connections using the vias 1020 can enable the use of a smaller number of flexible interconnects for specific purposes. This system of hybrid connections enables a wide variety of electronics to be utilized.

The cable 1060 can be, for example and not limitation, a flexible interconnect. In some embodiments, the cable 1060 can be disposed in the guide wire opening 1050. In this configuration, the cable 1060 does not contribute to the exterior size and shape of the probe 1055. In other embodiments the cable 1060 can be threaded through an open via 1020 in the silicon chip 1010 so that the guide wire opening 1050 is not obstructed.

While several possible embodiments are disclosed above, embodiments of the present invention are not so limited. For instance, while several possible configurations of materials have been disclosed, other suitable materials and combinations of materials could be selected without departing from the spirit of embodiments of the invention. In addition, the location and configuration used for various features of embodiments of the present invention can be varied according to a particular application or imaging technology that requires a slight variation due to, for example, the materials used and/or space or power constraints. Such changes are intended to be embraced within the scope of the invention.

While the various embodiments of this invention have been described in detail with particular reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all applicable equivalents.

We claim:

1. An integrated circuit comprising:
a first silicon chip comprising one or more capacitive micromachined ultrasonic transducers (CMUTs) and one or more complementary metal-oxide-semiconductor (CMOS) electronic devices;
a second silicon chip comprising one or more electronic devices; and
one or more through silicon vias (TSVs) disposed in the first silicon chip;
wherein the first silicon chip and the second silicon chip are electrically connected using the one or more TSVs.

2. The integrated circuit of claim 1, wherein the CMOS electronic devices comprise one or more buffers.

3. The integrated circuit of claim 1, wherein the CMOS electronic devices comprise one or more multiplexers.

4. The integrated circuit of claim 1, wherein the CMOS electronic devices comprise one or more amplifiers.

5. The integrated circuit of claim 1, wherein the one or more CMUTs are printed directly on top of, and in electrical communication with, the one or more CMOS electronic devices.

6. The integrated circuit of claim 1, further comprising:
one or more printed circuit traces for electrically connecting the one or more CMUTs, the one or more CMOS electronic devices, or both, to the one or more TSVs.

7. A method of manufacturing an integrated circuit comprising:
fabricating one or more complementary metal-oxide-semiconductor (CMOS) electronic components to form a CMOS electronics layer on a front side of a substrate;
depositing protection layer over the CMOS electronic components;
etching one or more through silicon vias (TSVs) through the substrate;
depositing dielectric material into the one or more TSVs;
electroplating the one or more TSVs to form electrical connections from the front side of the substrate to a back side of the substrate;
etching an isolation layer on the CMOS electronics layer to enable electrical connections to the CMOS electronics;
fabricating one or more capacitive micromachined ultrasonic transducer (CMUT) components on the isolation layer such that the CMUT electronic components are in electrical contact with the CMOS electronic components.

8. The method of claim 7, wherein protection layer is an oxide or nitride based protection layer.

9. The method of claim 7, wherein the etching step further comprises:
etching one or more electrical pathways to enable connection between one or more of the CMOS electronic components, the CMUT components, or both, and the TSVs.

10. The method of claim 9, further comprising:
fabricating one or more metal traces for connecting one or more of the CMOS electronic components, the CMUT components, or both to the TSVs.

11. The method of claim 7, further comprising:
fabricating one or more electronic components on the back side of the substrate;
connecting the one or more electrical components to the back side of the TSVs.

12. The method of claim 11, further comprising connecting one or more cables to the back side of the TSVs for inputting signals to, and outputting signals from, the integrated circuit.

13. An integrated circuit comprising:
a first silicon chip comprising a front side of a substrate and a back side of a substrate;
one or more capacitive micromachined ultrasonic transducer (CMUT) devices disposed on the front side of the substrate;
one or more complementary metal-oxide-semiconductor (CMOS) electronic devices disposed on the front side of the substrate and in electrical communication with the one or more CMUT devices; and
one or more through silicon vias (TSVs) for enabling one or more connections between the front side of the substrate and the back side of the substrate.

14. The integrated chip of claim 13, wherein at least one of the one or more TSVs are filled with a conductive material to provide one or more electrical connections between the front side of the substrate and the back side of the substrate.

15. The integrated chip of claim 13, wherein at least one of the one or more TSVs further comprise a flex tape connection for providing and electrical connection between the front side of the substrate and the back side of the substrate.

16. The integrated chip of claim 13, wherein at least one of the one or more CMOS electronic devices comprises a multiplexer for combining two or more outputs from the CMUT devices, the CMOS electronic devices, or both, into a single output.

17. The integrated chip of claim 13, wherein at least one of the one or more CMOS electronic devices comprises an amplifier.

18. The integrated circuit of claim 13, further comprising:
one or more printed circuit traces for electrically connecting the one or more CMUT devices, the one or more CMOS electronic devices, or both, to the one or more TSVs.

19. The integrated circuit of claim 13, wherein the one or more TSVs are disposed on empty portions of the substrate.

* * * * *